US00PP14924P2

(12) United States Plant Patent
Houbraken

(10) Patent No.: US PP14,924 P2
(45) Date of Patent: Jun. 22, 2004

(54) *SANVITALIA SPECIOSA* PLANT NAMED 'SANTANIS' (S&G 20032)

(50) Latin Name: *Sanvitalia×hybrida*
Varietal Denomination: Santanis (S&G 20032)

(75) Inventor: Anna M. W. P. Houbraken, Enkhuizen (NL)

(73) Assignee: Syngenta Seeds B.V., Enkhuizen (NL)

( * ) Notice: Subject to any disclaimer, the term of this patent is extended or adjusted under 35 U.S.C. 154(b) by 27 days.

(21) Appl. No.: 10/342,895

(22) Filed: Jan. 15, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Michelle Kizilkaya
(74) *Attorney, Agent, or Firm*—Bruce Vrana; Edouard G. Lebel

(57) ABSTRACT

A distinct cultivar of Sanvitalia plant named 'Santanis' (S&G 20032) which is particularly distinguished by its very compact plant habit, ball shape, small flowers and constant floridity during summer.

1 Drawing Sheet

Latin name of the genus and species of the plant claimed: *Sanvitalia×hybrida*.
Varietal denomination: 'Santanis' (S&G 20032).

BACKGROUND OF THE NEW PLANT

The present invention comprises a new distinct cultivar of Sanvitalia, botanically known as *Sanvitalia×hybrida*, native to South USA and Mexico. The new cultivar is propagated by cuttings resulting from a seedling from female plant *Sanvitalia×hybrida* identified as number 'A 178A-1.' The male parent is unidentified as the seeding was a result of a non-controlled pollination.

DESCRIPTION OF THE DRAWING

This new Sanvitalia plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new Sanvitalia plant. The data which defines these characteristics were collected from asexual reproductions carried out in Enkhuizen, Netherlands. The plant history was taken on 25 weeks old plants, grown in an open field in Enkhuizen, Netherlands with day and night temperatures ranges from 15 to 30 degrees Centigrade, and night temperatures ranging from 5 to 18 degrees Centigrade.

Asexual reproduction of the new cultivar taken in a controlled environment in Enhuizen, Netherlands since September 2000 has shown that the unique features of this new Sanvitalia are stable and reproduced true to type in successive generations.

Color references are primarily to The R.H.S. Colour Chart of The Royal Horticultural Society of London.

Comparison Between the New Cultivar 'Santanis,' its Parent and a Similar Cultivar

| | 'Santanis' (S & G 20032) | 'A 178A-1' (unpatented) | 'Sunbini' (unpatented) |
|---|---|---|---|
| Flower size | 1.3–1.6 | 1.1–1.3 | 1.3–1.4 |
| Plant height | 15 cm | 18 cm | 20 cm |
| Plant width | 35 cm | 35 cm | 35 cm |
| Internode length | 3 cm | 5 cm | 4 cm |
| Leaf color | 139A | 133A | 137A |
| Leaf attachment | Normal | Normal | Twisted |

The plant:

*Classification*.—Botanical: *Sanvitalia×hybrida* cv. 'Santanis'.

Parentage:

*Female parent*.—Seedling selection of *Sanvitalia×hybrida*, identified under number 'A 178A-1,' (unpatented).

*Male parent*.—Unidentified selection of Santivalia× hybrida (unpatented).

Propagation:

*Type of cuttings*.—Terminal cuttings.

*Time to initiate roots*.—14 days at air temperature of 21 degrees Centigrade.

*Time to develop roots*.—21 days at air temperature of 17 degrees Centigrade.

Plant description:

*Growth habit*.—Very compact growing, almost creeping, bit trailing.

*Plant height*.—15 cm.

*Vigour*.—Medium.

*Spreading area of plant*. —35–40 cm.

*Strength*.—Good tolerance to heat and cold conditions and diseases and pests.

*Branching character*.—Freely branching without pinching.

*Quantity of branches*.—30 branches per plant.

*Crop time*.—14 weeks to flowering from good developed rooted cutting.

The stem:
*Diameter*.—2 mm.
*Shape*.—Cylindrical.
*Anthocyan pigmentation*.—Slightly present in older stems 166A.
*Length of internode*.—20–40 mm depending on light conditions. $1^{st}$ 20 mm, $2^{nd}$ 30 mm, $3^{rd}$ 40 mm.
*Pubescence*.—Absent.
*Color*.—Young stem: 146C. Older stem: 187A The foliage:
*Phyllotaxis*.—Opposite.
*Shape of leaf*.—Lanceolate.
*Leaf apex*.—Rounded.
*Leaf base*.—Rounded.
*Texture*.—Sturdy hairy leaves.
*Leaf length*.—1–2 cm.
*Leaf width*.—0.4–0.7 cm.
*Depth of incision*.—No incision.
*Color*.—Upper side: 139A. Lower side: 137C.
*Pubescence*.—Little hairy.
*Petiole*.—Length: No.
*Venation*.—Shape: Pinnate. Color: 137B.
*Leaf anthocyanin coloration*.—137A.

The flower bud:
*Peduncle length*.—1.6–2.5 cm.
*Pubescence on peduncle*.—Many pubescent soft hairs, 2 mm long.
*Size of the bud*.—Length: 0.3 cm. Diameter: 0.3–0.5 cm.
*Shape*.—Ball shape.
*Color*.—144B.

Inflorescence:
*Diameter*.—1.3–1.6 cm.
*Form*.—Capitulum with 1 series of ray florets and more series of Disc florets.
*Overlapping of ray florets*.—No overlapping.
*Receptacle*.—Shape: Convex. Height: 2 mm. Color: 144A.
*Involucre*.—5 bracts in 1 series.
*Color*.—144A
*Fragrance*.—Absent.
*Number of flowers per plant*.—700 flowers per plant.
*Lastingness of flowers*.—±25 days.

Ray florets:
*Number of ray florets per inflor*.—13.
*Size*.—Length: 5 mm. Width: 2 mm.
*Shape of florets*.—Ovate.
*Color*.—12A.

Disc florets:
*No. of disc florets per inflor*.—>100.
*Size*.—Length: 2 mm. Width: 1 mm.
*Shape of florets*.—Tubular.
*Color*.—153B.

Androecium:
*Anther color*.—153B.
*Pollen color*.—7A.
*Amount of pollen*.—Few Pollen.

Gynoecium:
*Pistil number*.—1 in each floret.
*Style color*.—12A.
*Stigma color*.—12A.

Seed:
*Production*.—10–13 seeds per capitulum.
*Size*.—Length: 2 mm. Width: 1 mm.
*Color*.—N199A.

Physiological and ecological characteristics:
*Good tolerance to heat*.—Strong resistance to pests and diseases.

What is claimed is:

1. A new and distinct variety of Sanvitalia plant, substantially as illustrated and described herein.

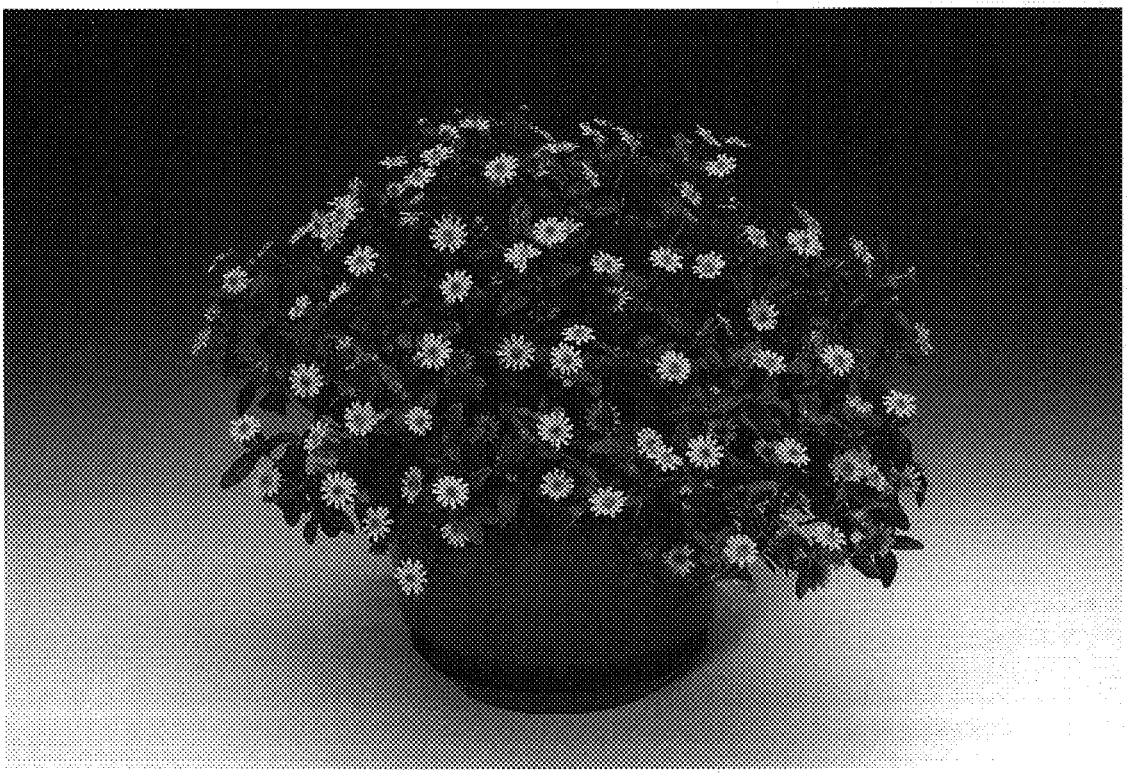

* * * * *